United States Patent
Li et al.

(10) Patent No.: US 12,121,388 B2
(45) Date of Patent: Oct. 22, 2024

(54) ENERGY-BASED SCATTER FRACTION ESTIMATION AND SCATTER CORRECTION

(71) Applicant: CANON MEDICAL SYSTEMS CORPORATION, Tochigi (JP)

(72) Inventors: Xiaoli Li, Vernon Hills, IL (US); Yi Qiang, Vernon Hills, IL (US); Wenyuan Qi, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 252 days.

(21) Appl. No.: 17/886,716

(22) Filed: Aug. 12, 2022

(65) Prior Publication Data

US 2024/0050058 A1  Feb. 15, 2024

(51) Int. Cl.
*A61B 6/00* (2024.01)
*A61B 6/03* (2006.01)
*G06T 11/00* (2006.01)

(52) U.S. Cl.
CPC ............ *A61B 6/5282* (2013.01); *A61B 6/037* (2013.01); *G06T 11/005* (2013.01); *G06T 2211/424* (2013.01)

(58) Field of Classification Search
CPC ..... A61B 6/5282; A61B 6/037; A61B 6/4241; A61B 6/482; A61B 6/483; A61B 6/5205; G06T 11/005; G06T 2211/424
See application file for complete search history.

(56) References Cited

U.S. PATENT DOCUMENTS

| | | | | |
|---|---|---|---|---|
| 5,489,782 | A * | 2/1996 | Wernikoff | G01N 23/083 250/371 |
| 6,490,476 | B1 * | 12/2002 | Townsend | G01T 1/2985 250/363.04 |
| 2001/0040219 | A1 * | 11/2001 | Cherry | G01T 1/2985 250/363.03 |
| 2002/0143249 | A1 * | 10/2002 | Tornai | A61B 6/502 600/425 |
| 2008/0131362 | A1 * | 6/2008 | Rousso | A61M 5/1782 424/1.11 |
| 2008/0277587 | A1 * | 11/2008 | Case | G01T 1/1648 250/363.07 |

(Continued)

OTHER PUBLICATIONS

Gómez et al.; "Fast Energy Dependent Scatter Correction for List-Mode PET Data", Journal of Imaging, Sep. 30, 2021.

*Primary Examiner* — Kiho Kim
(74) *Attorney, Agent, or Firm* — Oblon, McClelland, Maier & Neustadt, L.L.P.

(57) ABSTRACT

A method is provided for determining a scatter fraction for a radiation diagnosis apparatus. The method includes acquiring an energy spectrum from list mode data obtained from a scan performed using the radiation diagnosis apparatus; determining, from the acquired list mode data, a first number of events occurring in a first energy window spanning a first energy range; determining, from the acquired list mode data, a second number of events occurring in a second window, the second energy window spanning a second energy range different from the first energy range; calculating a singles scatter fraction based on the determined first number of events and the determined second number of events; and reconstructing an image based on the acquired list mode data and the calculated singles scatter fraction.

20 Claims, 6 Drawing Sheets

(56) References Cited

U.S. PATENT DOCUMENTS

| | | | |
|---|---|---|---|
| 2009/0078876 A1* | 3/2009 | Chinn | G01T 1/2985 250/363.04 |
| 2010/0174180 A1* | 7/2010 | Rousso | G16H 30/40 600/431 |
| 2013/0216113 A1* | 8/2013 | O'Connor | A61B 6/4258 382/128 |
| 2013/0248719 A1* | 9/2013 | Volokh | A61B 6/5258 250/362 |
| 2016/0209524 A1 | 7/2016 | Laurence et al. | |
| 2021/0030387 A1 | 2/2021 | Andreyev et al. | |
| 2021/0279917 A1 | 9/2021 | Wilk | |
| 2021/0375009 A1 | 12/2021 | Ye et al. | |

* cited by examiner

ENERGY-BASED SCATTER FRACTION ESTIMATION AND SCATTER CORRECTION

BACKGROUND

Field

The present disclosure relates to scatter fraction estimation and scatter correction in nuclear medicine devices, including Positron Emission Tomography (PET) diagnostic devices.

Description of the Related Art

Compton scattering in a PET scan of a patient degrades the image quality of a reconstructed PET image by substantially reducing the contrast of the reconstructed PET image. In particular, Compton scattering reduces the accuracy of activity quantitation, so that scatter correction is a vital process in producing high-resolution, artifact-free quantitative PET images. Moreover, scatter fraction estimation is an important step in the process of scatter correction, and an important performance metric of a PET scanner.

Conventionally, a number of PET scatter-correction algorithms have been proposed to reduce image-contrast degradation and quantitative accuracy loss. For example, an analytic-model-based scatter correction algorithm generally uses both PET/CT data and a mathematical model of the scanner that incorporates the physics of Compton scattering (e.g., using the Klein-Nishina formula). However, the analytic-model-based method can be inaccurate due to improper scaling of the estimated scatter sinogram with respect to the measured data. Recent improvements to energy resolution and the list-mode data storage of PET data have allowed the use of energy-based scatter correction.

However, existing scatter correction algorithms have several drawbacks. First, the analytic-model-based scatter correction algorithm is often less accurate because multiple-scattering is neglected to improve calculation speed, and proper scaling of the estimated scatter sinogram is challenging. Further, while energy-based scatter correction algorithms are practical, they are typically less accurate.

SUMMARY

The present disclosure provides a practical and accurate scatter-fraction-estimation algorithm for detected singles events for an overall nuclear medicine scanner having multiple detectors, for each crystal in the scanner, and/or for each group of crystals in the scanner. The more accurate singles scatter fraction for the scanner improves the scatter correction accuracy when using the analytic-model-based scatter correction. The calculation of the singles scatter fraction for each crystal or each group of crystals can be used to perform scatter correction directly in the reconstruction process.

An embodiment of the present disclosure is directed to a method for determining a scatter fraction for a radiation diagnosis apparatus. The method includes acquiring an energy spectrum from list mode data obtained from a scan performed using the radiation diagnosis apparatus; determining, from the acquired list mode data, a first number of events occurring in a first energy window spanning a first energy range; determining, from the acquired list mode data, a second number of events occurring in a second window, the second energy window spanning a second energy different from the first energy range; calculating a singles scatter fraction based on the determined first number of events and the determined second number of events; and reconstructing an image based on the acquired list mode data and the calculated singles scatter fraction.

Another embodiment of present disclosure is directed to an apparatus for determining a scatter fraction for a radiation diagnosis apparatus. The apparatus includes circuitry configured to acquire an energy spectrum from list mode data obtained from a scan performed using the radiation diagnosis apparatus; determine, from the acquired list mode data, a first number of events occurring in a first energy window spanning a first energy range; determine, from the acquired list mode data, a second number of events occurring in a second window, the second energy window spanning a second energy range different from the first energy range; calculate a singles scatter fraction based on the determined first number of events and the determined second number of events and reconstruct an image based on the acquired list mode data and the calculated singles scatter fraction.

A further embodiment of present disclosure is directed to a system, comprising a radiation diagnosis apparatus configured to perform a scan of a patient to obtain list mode data. The system further includes circuitry configured to acquire an energy spectrum from the obtained list mode data; determine, from the acquired list mode data, a first number of events occurring in a first energy window spanning a first energy range; determine, from the acquired list mode data, a second number of events occurring in a second window, the second energy window spanning a second energy range different from the first energy range; calculate a singles scatter fraction based on the determined first number of events and the determined second number of events and reconstruct an image based on the acquired list mode data and the calculated singles scatter fraction.

BRIEF DESCRIPTION OF THE DRAWINGS

The application will be better understood in light of the description which is given in a non-limiting manner, accompanied by the attached drawings in which.

DETAILED DESCRIPTION

Figure 2A:
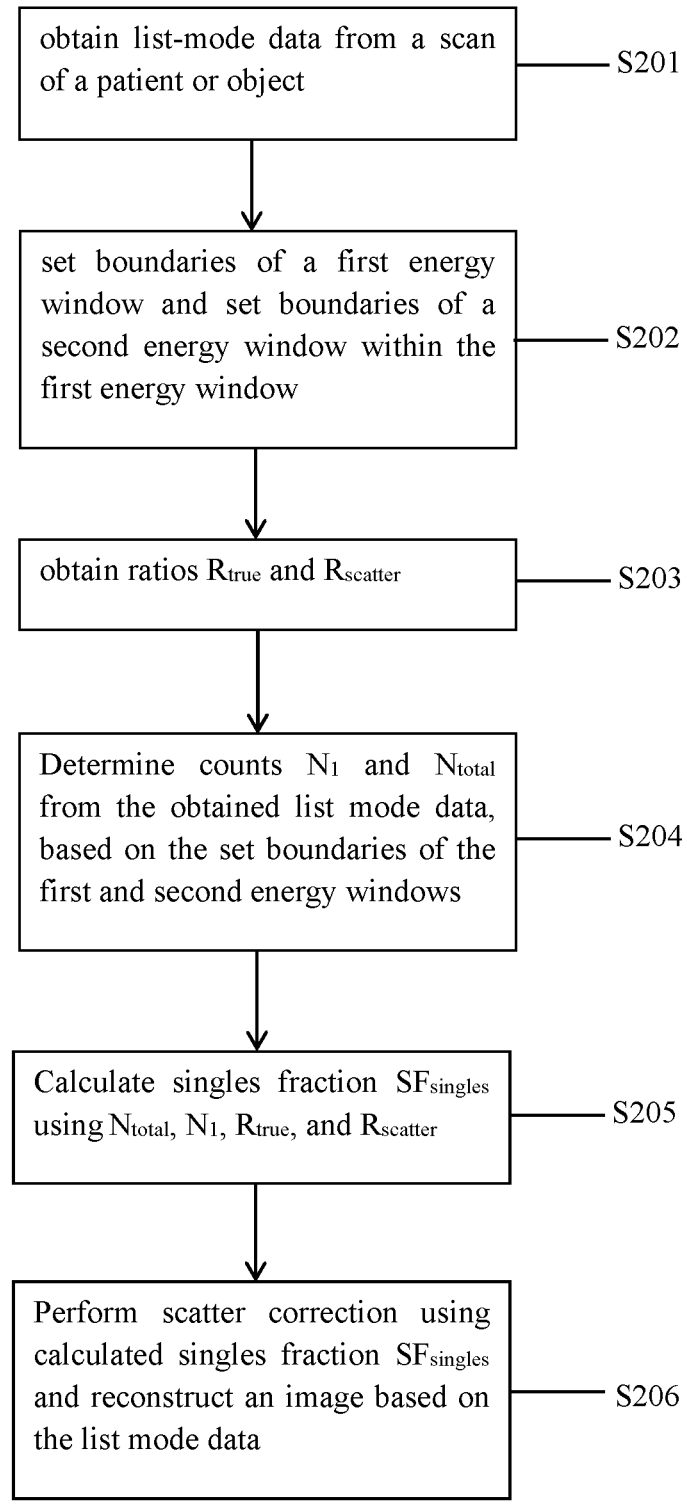
FIG. 2A is a flowchart of a method of performing scatter fraction estimation according to one embodiment of the present disclosure.

As shown in the flowchart of FIG. 2A, in one embodiment, the singles scatter fraction is estimated for the overall scanner, for each crystal, and/or for each group of crystals from energy spectra formed using list-mode data, after subtraction of random events. In particular, the singles scatter fraction is estimated from the number of coincidence events within the photopeak energy window and also within a second energy window, such as a high-energy window above 511 keV (e.g., 530-580 keV). In this embodiment, no direct comparison of energy spectra or fitting to an energy spectra is required. Further, in this embodiment, the coincidence scatter fraction for the scanner is calculated from the determined singles scatter fraction for the scanner. In one example, the coincidence scatter fraction for the scanner is estimated from the determined singles scatter fraction for the scanner, and then is used to properly scale the estimated scatter sinogram, when using the analytic-model-based scatter correction. In an alternative embodiment, the determined singles scatter fraction for each crystal or each group of crystals is used to perform scatter correction directly during the reconstruction process.

In step S201, list mode data of a PET scan of a patient is obtained.

Figure 1:
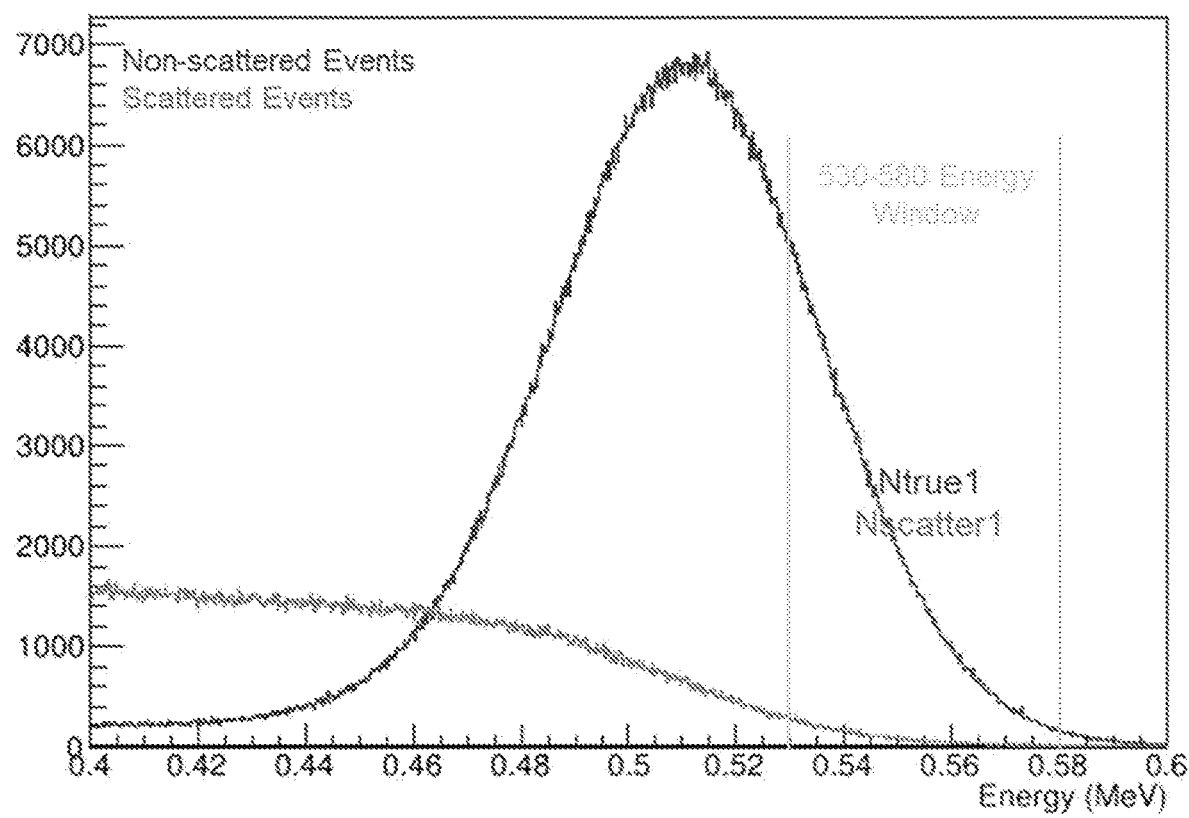
FIG. 1 is a diagram of a simulated system coincidence energy spectra showing scatter events and true events within a photopeak window.

In step S202, the photopeak window and the second energy window within the photopeak window are set. As shown in the example of FIG. 1, the second energy window is set to be between 530-580 keV and the photopeak window is 400-600 keV. However, these are only example energy ranges, and other energy ranges can be used to define the photopeak window and the second energy window within the photopeak window.

As shown in FIG. 1, $N_{scatter1}$ is defined as the number of scatter events in the photopeak window inside the second energy window. Further, $N_{scatter2}$ can be defined as the number of scatter events inside the photopeak window outside the second energy window, and $N_{scatter}N_{scatter1}+N_{scatter2}$ is defined as the total number of scatter events in the photopeak window.

Similarly, as shown in FIG. 1, $N_{true1}$ is defined as the number of true events in the second energy window. Further, $N_{true2}$ can be defined as the number of true events in the photopeak window outside the second energy window, and $N_{true}=N_{true1}+N_{true2}$ is the total number of true events in the photopeak window.

Finally, $N_1=N_{true1}+N_{scatter1}$ is defined as the number of scatter and true events inside the second energy window, while $N_{total}=N_{true}+N_{scatter}$ is defined as the total number of scatter and true events within the photopeak window. Note that the above defined counts can be defined per crystal i, per group of crystals, or for the entire scanner, for example.

In step S203, predetermined values for the ratios $R_{true}=N_{true1}/N_{true}$ and $R_{scatter}=N_{scatter1}/N_{scatter}$ are acquired. In particular, $R_{true}$, the ratio of the number of true events within the second energy window to the number of true events within the photopeak window can be estimated from point source or line source data, by simulation, or by measurement. Similarly, $R_{scatter}$, the ratio of the number of scatter events within the second energy window to the number of scatter events within the photopeak window can be estimated by simulation. The estimation of $R_{true}$ and $R_{scatter}$ can occur any time prior to obtaining the list mode data and can be pre-stored in a memory. Thus, Step S203 can be performed prior to steps S201 and S202. Note that due to events pileup during high-activity periods and possible background radiation in crystals, the energy spectra could be different at different periods, so that $R_{true}$ and $R_{scatter}$ can be activity dependent.

In step S204, $N_1$ and $N_{total}$ are calculated from the list mode data obtained in step S201 based on the photopeak window and the second energy window set in step S202.

In step S205, the singles scatter fraction is calculated. In particular, from the above relationships between count rates, measured count rates, and estimated ratios $R_{true}$ and $R_{scatter}$, the number of scatter events in the second energy window is calculated as:

$$N_{scatter1} = \frac{Ntotal \cdot Rtrue - N1}{Rtrue - Rscatter} R_{scatter}.$$

Thus, the number of scatter events within the photopeak window is:

$$N_{scatter} = \frac{N_{scatter1}}{R_{scatter}} = \frac{Ntotal \cdot Rtrue - N1}{Rtrue - Rscatter}.$$

Finally, the singles scatter fraction for the scanner (or each crystal i or group of crystals) is calculated as $SF_{singles}=N_{scatter}/N_{total}$.

Further, in step S205, the coincidence scatter fraction for the scanner ($SF_{coincidence}$) can be approximately calculated from the singles scatter fraction $SF_{singles}$ for the scanner using the equation $SF_{coincidence}=1-(1-SF_{singles})^2$.

In step S206, the calculated coincidence scatter fraction for the scanner $SF_{coincidence}$ is used to normalize the estimated scatter sinogram when using the analytic-model-based scatter correction algorithm to perform scatter correction, and reconstruct an image.

For example, in the ML-EM algorithm for PET, the iterative update equation is:

$$\bar{f}_j^{k+1} = \frac{\bar{f}_j^k}{\sum_i H_{ij}} \sum_i H_{ij} \frac{g_i}{\sum_{n=0}^{N-1} H_{in} \bar{f}_n^k}$$

where $g_i$ are the measured counts in the ith LOR, and $\bar{f}_j^k$ is the estimated activity in jth voxel at kth iteration. Then, the iterative update equation with scatter correction is:

$$\bar{f}_j^{k+1} = \frac{\bar{f}_j^k}{\sum_i H_{ij}} \sum_i H_{ij} \frac{g_i}{\sum_{n=0}^{N-1} H_{in} \bar{f}_n^k + s_i}$$

where $s_i$ is the estimated scatter.

There are several possible ways to estimate scatter, such as singles scatter simulation (SSS), but SSS should be implemented with tail-fitting in order to make sure the estimated scatter has the correct scaling. Moreover, tail-fitting can fail when the tail region is small, or the data is noisy. However, the SF value estimated to the disclosed embodiments can be used for scatter scaling. For example, if the estimated scatter from SSS is $\hat{s}_i$, then $$s_i = \frac{\hat{s}_i}{S} * G * SF,$$

where G and S are the sum of all the elements of measurement prompts and estimated scatter from SSS.

Figure 2B:
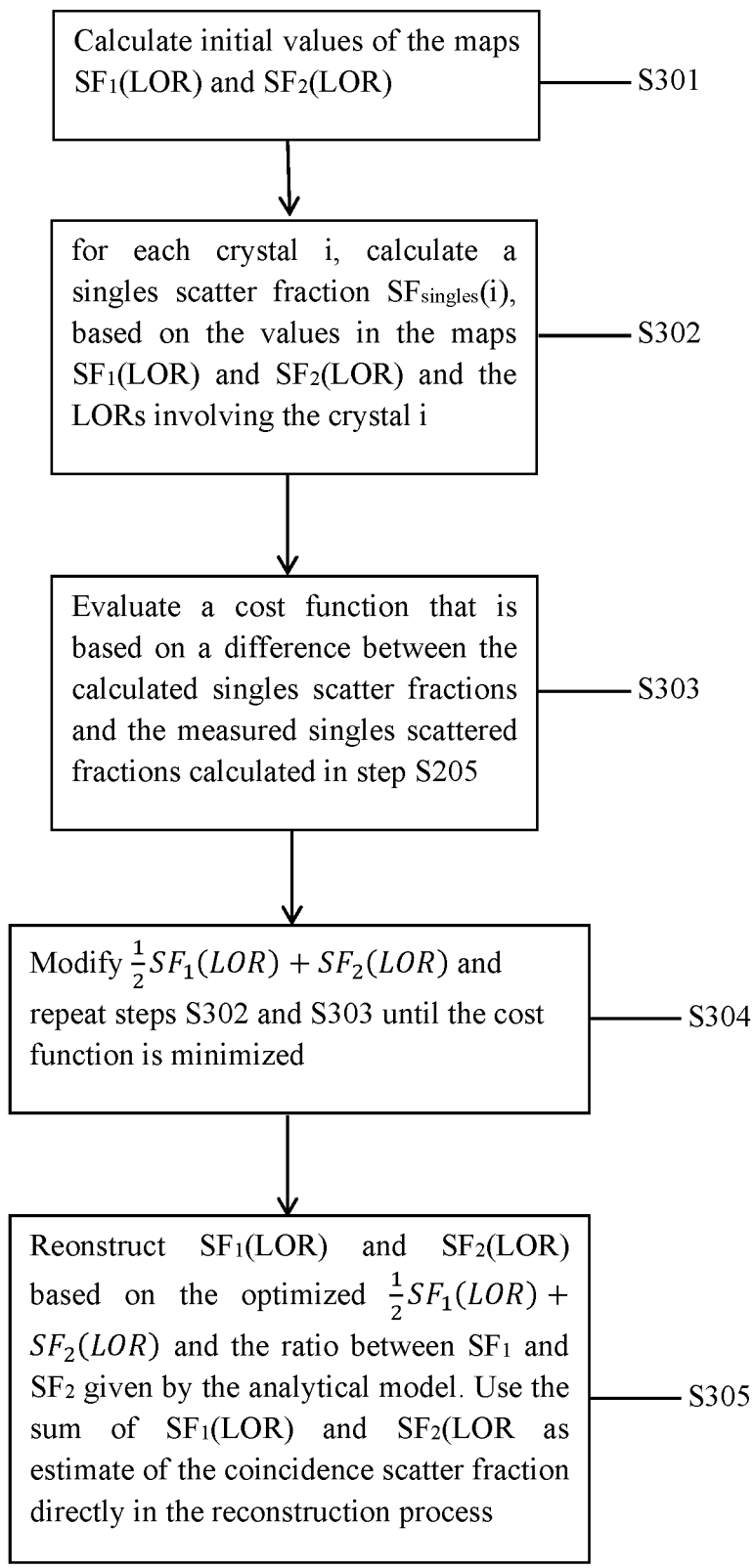
FIG. 2B a flowchart of a method of performing scatter correction according to one embodiment of the present disclosure.

Alternatively, in step S206, the singles scatter fraction $SF_{singles}$ for each crystal or each group of crystals is used to perform scatter correction directly, accordingly to the steps shown in the flowchart of FIG. 2B. In one embodiment, the number of crystals to group together for scatter fraction estimation can be determined based on the count rate.

The method of FIG. 2B uses two coincidence scatter fraction maps in a coordinate system defined by the lines of response (LOR), or sinograms. The first map, $SF_1(LOR)$, describes the fraction of single-scattered coincidence events, i.e., when only one 511 keV photon is scattered. The second map, $SF_2(LOR)$, describes the fraction of double-scattered coincidence events, i.e., when both 511 keV photons are scattered. Both maps can use coarser bins, as the scatter fraction has a smoother distribution when the singles scatter fraction is calculated for each group of crystals.

In step S301, the initial values of the maps $SF_1(LOR)$ and $SF_2(LOR)$ are calculated using a physics-based analytical model, and CT images or non-scatter-corrected PET images. In one example, a scattering simulation is executed given scattering cross-section, scanner geometry, detector efficiency, 511 keV photon emission density, and the attenuation map based on the scanner object. For each LOR, the simulated events are classified into three categories, $N_{non-scatter}$, $N_{1-scatter}$, $N_{2-scatter}$. The scattering factions can then be calculated accordingly to $SF_1(LOR)=N_{1-scatter}/(N_{non-scatter}+N_{1-scatter}+N_{2-scatter})$ and $SF_2(LOR)=N_{2-scatter}/(N_{non-scatter}+N_{1-scatter}+N_{2-scatter})$.

In step S302, for each crystal i (or a group of crystals), a theoretical singles scatter fraction $SF_{singles}(i)$ is calculated, based on (1) the maps $SF_1(LOR)$ and $SF_2(LOR)$, (2) the total number of events reaching crystal i, and (3) for each LOR involving crystal i, the number of events for the LOR, as follows:

$$SF_{singles}(i) = \frac{\sum \text{all } LOR_j \text{ involving Crystal}_i \text{ Number of events in } LOR_j \times \left(\frac{1}{2}SF_1(LOR_j) + SF_2(LOR_j)\right)}{\text{Total number of Events Reaching Crystal}_i}$$

In step S303, a cost function is evaluated. The cost function is constructed as a difference between the calculated theoretical singles scatter fractions determined in S302 and the measured singles scattered fractions (from step S205).

In step S304, the values $$\frac{1}{2}SF_1(LOR) + SF_2(LOR)$$

are modified and steps S302 and S303 are repeated until the cost function is minimized and optimal values of $$\frac{1}{2}SF_1(LOR) + SF_2(LOR)$$

are found. In the optimization process, constraints can be imposed to ensure meaningful results, e.g. $SF_1(LOR)+SF_2(LOR) \leq 1$ in general, and $SF_1(LOR)+SF_2(LOR)=1$ when outside the patient.

In step S305, after the optimization process is completed, $SF_1(LOR)$ and $SF_2(LOR)$ are determined based on the optimized values of $$\frac{1}{2}SF_1(LOR) + SF_2(LOR)$$

and based on the ratio between $SF_1$ and $SF_2$ given by the analytical model. In an alternative embodiment, $SF_1(LOR)$ and $SF_2(LOR)$ are also smoothed to reduce noise.

In one embodiment, the sum of $SF_1(LOR)$ and $SF_2(LOR)$, is used as an estimate of the coincidence scatter fraction directly in the reconstruction process.

In another embodiment, three-dimensional scatter fraction maps can be used.

Figure 3:
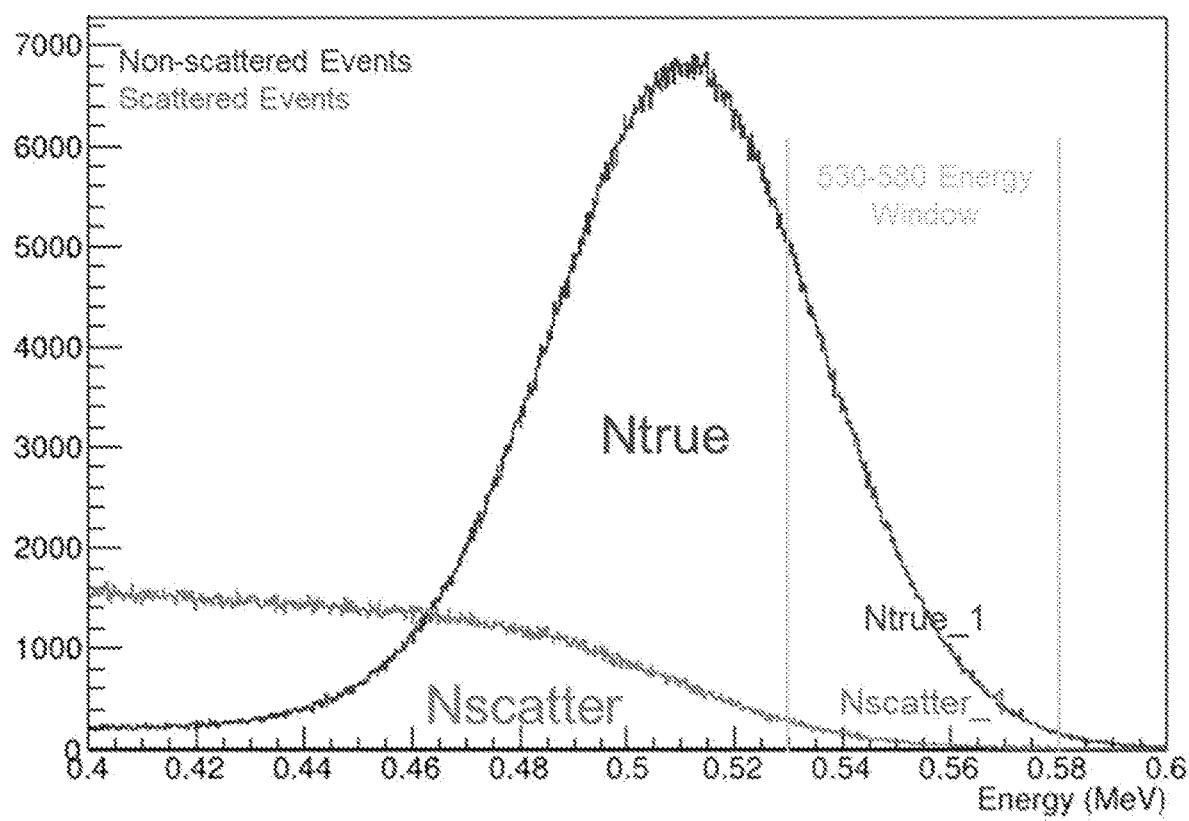
FIG. 3 is a diagram of a simulated system coincidence energy spectra showing scatter events and true events within a photopeak window according to an alternative embodiment.

An alternative embodiment, as shown in FIG. 3, the location of the second window is generalized, and can be within, overlapping, or outside the photopeak (PE) window. In this embodiment, the following "known" values can be obtained: (1) N is the total number of measured events within the PE window, (2) $N_1$ is the total number of measured events within the second window, (3) $R_{scatter}$ is $N_{scatter1}/N_{scatter}$ and is obtained via simulation, for example, and (4) $R_{true}$ is $N_{scatter1}/N_{true}$ and is obtained from line/point source measurements or simulation, for example.

In this embodiment, the generally unknown values are: (1) $N_{scatter}$, the number of scatter events within the PE window, (2) $N_{scatter1}$, the number of scatter events within the second window, (3) $N_{true}$, the number of true events with the PE window, (4) $N_{true1}$, the number of true events in the second window, and (5) SF, which is $N_{scatter}/N$, the scattering fraction within the PE window. However, the scatter fraction can be calculated as:

$$SF = \frac{R_{true} - \frac{N_1}{N}}{R_{true} - R_{scatter}}$$

Further, in this embodiment, the location and size of the second energy window can be determined by an optimization process to optimize the accuracy of the computed SF value. Further, additional energy windows could be used to improve the accuracy of the scattering fraction. For example, an SF value can be estimated using each of a plurality of the second energy windows, and the average of the estimated SF values could be used. Alternatively, an average SF value could be jointly fitted using data from all of the plurality of the second energy windows together. In alternative embodiment, the second energy window can be optimized by comparing the computed SF value with a known SF value from simulation data, or a well-studied phantom data, such as NEMA count rate phantom data.

The present disclosure includes scatter-correction methods and systems that provide several advantages over conventional approaches. First, the above-described methods are practical (i.e., fast and predictable), and accurately estimate the singles scatter fraction for the scanner, for each crystal, and/or each group of crystals from the number of coincidence events within the photopeak energy window and within a second energy window, e.g., above 511 keV (e.g., 530-580 keV). Further, no direct comparison of energy spectra or fitting to an energy spectra is required.

Moreover, the present disclosure provides a practical and accurate method to estimate the scanner scatter fraction from the singles scatter fraction for the scanner, which is used to normalize the estimated scatter sinogram when using an analytic-model-based scatter correction approach.

Further, the present disclosure provides a practical and accurate method to estimate the scatter fraction for each LOR from the singles scatter fraction for each crystal and/or each group of crystals, which is used to perform scatter correction directly during the reconstruction process.

Figure 4:
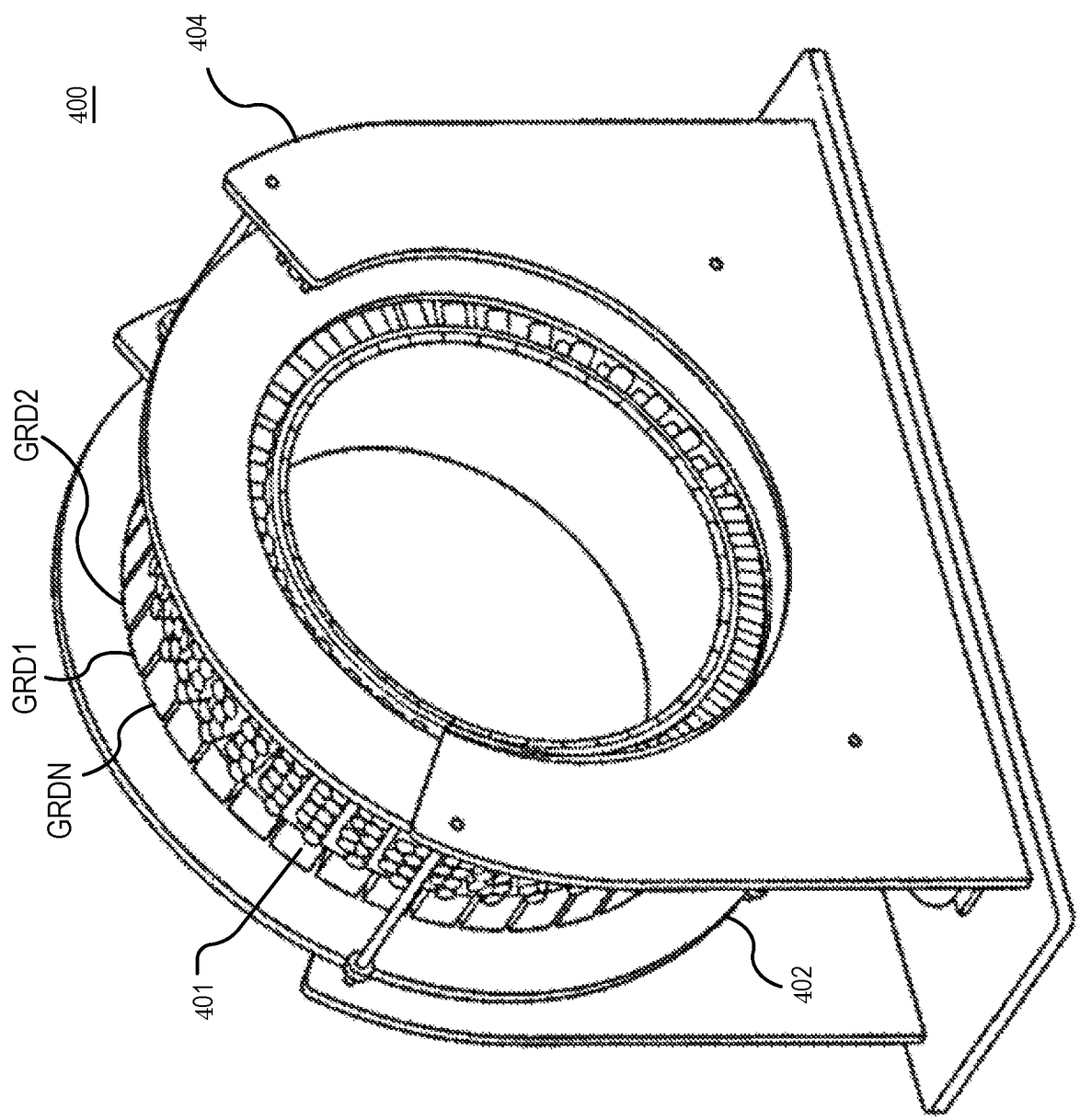
FIG. 4 is an illustration of a perspective view of a positron emission tomography (PET) scanner according to one embodiment of the present disclosure.
Figure 5:
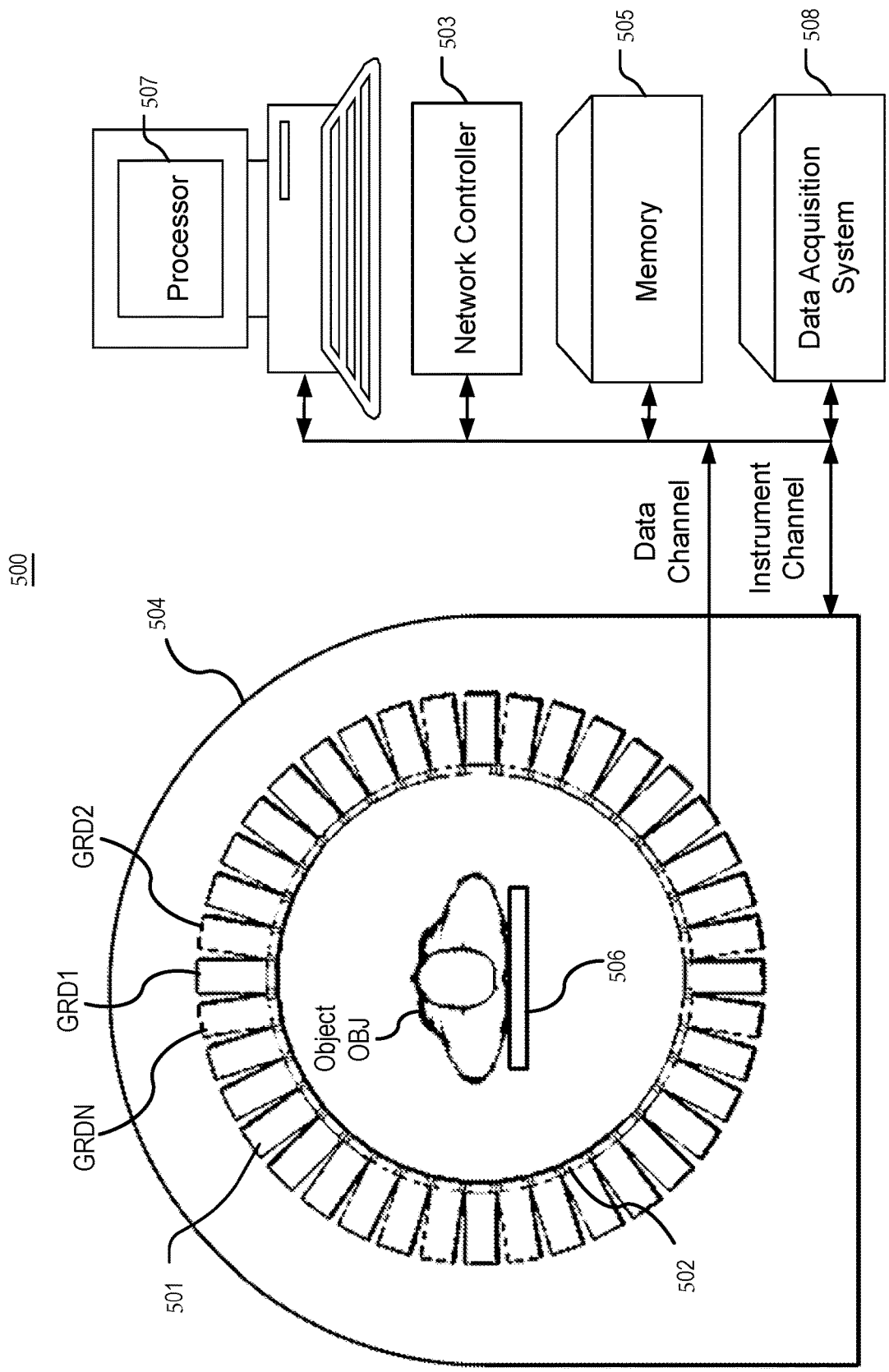
FIG. 5 is a schematic of a PET scanner apparatus and associated hardware, according to one embodiment of the present disclosure.

A PET scanner that can be used in the embodiments disclosed herein is shown in FIGS. 4 and 5. PET scanner 400 includes a plurality of gamma-ray detectors (GRDs) 401 (e.g., GRD1, GRD2, through GRDN) that are each configured as rectangular detector modules. According to one implementation, the detectors are arranged in a ring, which forms a circular bore 402 about a gantry 404. In this example, the ring includes 40 GRDs 401. A ring may have a different number of GRDs 401 depending on factors such as the desired size of bore 402. The GRDs 401 include scintillator crystal arrays for converting the gamma rays into scintillation photons (e.g., at optical, infrared, and ultraviolet wavelengths), which are detected by photodetectors. Each GRD 401 can include a two-dimensional array of individual detector crystals, which absorb gamma radiation and emit scintillation photons, or can include a monolithic array or a slatted array. The scintillation photons can be detected by a two-dimensional array of devices such as SiPMs (not shown) that are also arranged in the GRD 401. A light guide can be disposed between the array of detector crystals and the SiPMs. The crystal and SiPM arrangements according to the present disclosure are discussed in more detail below.

FIG. 4 shows a schematic view of a PET scanner system having GRDs arranged to detect gamma-rays emitted from an object OBJ. The GRDs can measure the timing, position, and energy corresponding to each detected gamma-ray. It can be appreciated that the single PET detector ring of FIG. 4 can be extrapolated to include any number of PET detector rings along an axial length of the PET scanner.

FIG. 5 shows an example of the arrangement of a PET scanner 500, in which the object OBJ to be imaged rests on a table 506 and the GRD modules GRD1 through GRDN are arranged circumferentially around the object OBJ and the table 506. The GRDs can comprise a PET detector ring and may be fixedly-connected to a circular bore 502 that is fixedly-connected to a gantry 504. The gantry 504 houses many parts of the PET scanner.

The gantry 504 of the PET scanner also includes an open aperture, defined by the cylindrical bore 502, through which the object OBJ and the table 506 can pass, and gamma-rays emitted in opposite directions from the object OBJ due to an annihilation event can be detected by the GRDs and timing and energy information can be used to determine coincidences for gamma-ray pairs.

In FIG. 5, circuitry and hardware are also shown for acquiring, storing, processing, and distributing gamma-ray detection data. The circuitry and hardware include a processor (processing circuitry) 507, a network controller 503, a memory 505, and a data acquisition system (DAS) 508. The PET imager also includes a data channel that routes detection measurement results from the GRDs to the DAS 508, the processor 507, the memory 505, and the network controller 503. The data acquisition system 508 can control the acquisition, digitization, and routing of the detection data from the detectors. In one implementation, the DAS 508 controls the movement of the table 506. The processor 507 performs functions including identifying arrangement errors, pre-reconstruction processing of the detection data, image reconstruction, and post-reconstruction processing of the image data.

According to an embodiment, the processor 507 of the PET scanner 500 of FIG. 5 can be configured to perform the methods as described herein. The processor 507 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory 505 can be a hard disk drive, CD-ROM drive, DVD drive, FLASH drive, RAM, ROM or any other electronic storage known in the art. The memory 505 may be non-volatile, such as ROM, EPROM, EEPROM or FLASH memory. The memory 505 can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 507 can execute a computer program including a set of computer-readable instructions that perform methods described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel or an Opteron processor from AMD and an operating system, such as Microsoft VISTA, UNIX, Solaris, LINUX, Apple, MAC-OS and other operating systems known to those skilled in the art. Further, the CPU can be implemented as multiple processors cooperatively working in parallel to perform the instructions. The instructions may be stored in memory 505 or within a memory located in network controller 503 (not shown).

In one implementation, the PET scanner may include a display for displaying a reconstructed image and the like. The display can be an LCD display, CRT display, plasma display, OLED, LED or any other display known in the art.

The network controller 503, such as an Intel Ethernet PRO network interface card from Intel, can interface between the various parts of the PET imager. Additionally, the network controller 503 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While the above embodiments are directed to a PET apparatus, the embodiments are also applicable to other position sensitive gamma detectors such as single-photon emission computerized tomography (SPECT).

Additional embodiments are provided by way of example in the following parentheticals.

(1) A method for determining a scatter fraction for a radiation diagnosis apparatus, the method comprising:
acquiring an energy spectrum from list mode data obtained from a scan performed using the radiation diagnosis apparatus;
determining, from the acquired list mode data, a first number of events occurring in a first energy window spanning a first energy range;
determining, from the acquired list mode data, a second number of events occurring in a second window, the second energy window spanning a second energy range different from the first energy range;

calculating a singles scatter fraction based on the determined first number of events and the determined second number of events; and reconstructing an image based on the acquired list mode data and the calculated singles scatter fraction.

(2) The method of (1), wherein the step of determining the first number of events comprises determining the first number of events occurring in the first energy window, which is a photopeak energy window that includes a photopeak energy level.

(3) The method of (2), wherein the step of determining the second number of events comprises determining the second number of events occurring in the second energy window spanning the second energy range, which lies entirely above the photopeak energy level.

(4) The method of (1) to (3), wherein
the step of calculating the singles scatter fraction comprises calculating the singles scatter fraction further based on a first ratio and a second ratio;
the first ratio is a ratio of a number of true events occurring within the second energy window to a number of true events occurring within the first energy window; and
the second ratio is a ratio of a number of scatter events occurring within the second energy window to a number of scatter events occurring within the first energy window.

(5) The method of (4), wherein the first ratio and the second ratio are pre-calculated and stored in a memory prior to obtaining the list mode data from the scan performed using the radiation diagnosis apparatus.

(6) The method of (5), further comprising estimating the first ratio and the second ratio from phantom data obtained either experimentally or via simulation.

(7) The method of (1) to (6), further comprising calculating a coincidence scatter fraction from the calculated singles scatter fraction.

(8) The method of (7), further comprising:
normalizing an estimated scatter sinogram using the calculated coincidence scatter fraction; and
performing scatter correction using the normalized scatter sinogram.

(9) The method of (1), wherein the calculating step further comprises calculating, for each crystal in the radiation diagnostic apparatus, a per-crystal singles scatter fraction; and
the method further includes
determining, from the calculated per-crystal singles scatter fractions, a first map and a second map, the first map indicating, for each of a plurality of lines of response (LORs), a fraction of single-scattered coincidence events, and the second map indicating, for each of the LORs, a fraction of double-scattered coincidence events;
estimating a coincidence scatter fraction from the determined first and second maps; and
using the estimated coincidence scatter fraction directly in a reconstruction process to reconstruct the image from the list mode data.

(10) The method of (9), wherein the step of determining the first map and the second map comprises performing an iterative optimization process to minimize a cost function that is based on the calculated per-crystal singles scatter fractions.

(11) The method of (1) to (10), wherein the calculating step further comprises calculating, for each group of a plurality of groups of crystals in the radiation diagnostic apparatus, a singles scatter fraction for the group.

(12) The method of (1) to (11), wherein the step of acquiring the energy spectrum further comprises subtracting random events from an initial energy spectrum.

(13) An apparatus for determining a scatter fraction for a radiation diagnosis apparatus, the apparatus comprising:
circuitry configured to
acquire an energy spectrum from list mode data obtained from a scan performed using the radiation diagnosis apparatus;
determine, from the acquired list mode data, a first number of events occurring in a first energy window spanning a first energy range;
determine, from the acquired list mode data, a second number of events occurring in a second window, the second energy window spanning a second energy range different from the first energy range;
calculate a singles scatter fraction based on the determined first number of events and the determined second number of events and
reconstruct an image based on the acquired list mode data and the calculated singles scatter fraction.

(14) The apparatus of (13), wherein the circuitry is further configured to, in determining the first number of events, determine the first number of events occurring in the first energy window, which is a photopeak energy window that includes a photopeak energy level.

(15) The apparatus of (14), wherein the circuitry is further configured to, in determining the second number of events, determine the second number of events occurring in the second energy window spanning the second energy range, which lies entirely above the photopeak energy level.

(16) The apparatus of (13) to (15), wherein
the circuitry is further configured to, in calculating the singles scatter fraction, calculate the singles scatter fraction further based on a first ratio and a second ratio;
the first ratio is a ratio of a number of true events occurring within the second energy window to a number of true events occurring within the first energy window; and
the second ratio is a ratio of a number of scatter events occurring within the second energy window to a number of scatter events occurring within the first energy window.

(17) The apparatus of (16), further comprising a memory, wherein the first ratio and the second ratio are pre-calculated and stored in the memory prior to obtaining the list mode data from the scan performed using the radiation diagnosis apparatus.

(18) The apparatus of (17), wherein the circuitry is further configured to estimate the first ratio and the second ratio from phantom data obtained either experimentally or via simulation.

(19) The apparatus of (13) to (18), wherein the circuitry is further configured to calculate a coincidence scatter fraction from the calculated singles scatter fraction.

(20) A system, comprising:
a radiation diagnosis apparatus configured to perform a scan of a patient to obtain list mode data; and circuitry configured to
  acquire an energy spectrum from the obtained list mode data;
  determine, from the acquired list mode data, a first number of events occurring in a first energy window spanning a first energy range;
  determine, from the acquired list mode data, a second number of events occurring in a second window, the second energy window spanning a second energy range different from the first energy range;
  calculate a singles scatter fraction based on the determined first number of events and the determined second number of events and
  reconstruct an image based on the acquired list mode data and the calculated singles scatter fraction.

Numerous modifications and variations of the present inventions are possible in light of the above teachings. It is therefore to be understood that within the scope of the appended claims, the inventions may be practiced otherwise than as specifically described herein.

The invention claimed is:

1. A method for determining a scatter fraction for a radiation diagnosis apparatus, the method comprising:
  acquiring an energy spectrum from list mode data obtained from a scan performed using the radiation diagnosis apparatus;
  determining, from the acquired list mode data, a first number of events occurring in a first energy window spanning a first energy range;
  determining, from the acquired list mode data, a second number of events occurring in a second window, the second energy window spanning a second energy range different from the first energy range;
  calculating a singles scatter fraction based on the determined first number of events and the determined second number of events; and
  reconstructing an image based on the acquired list mode data and the calculated singles scatter fraction.

2. The method of claim 1, wherein the step of determining the first number of events comprises determining the first number of events occurring in the first energy window, which is a photopeak energy window that includes a photopeak energy level.

3. The method of claim 2, wherein the step of determining the second number of events comprises determining the second number of events occurring in the second energy window spanning the second energy range, which lies entirely above the photopeak energy level.

4. The method of claim 1, wherein
  the step of calculating the singles scatter fraction comprises calculating the singles scatter fraction further based on a first ratio and a second ratio;
  the first ratio is a ratio of a number of true events occurring within the second energy window to a number of true events occurring within the first energy window; and
  the second ratio is a ratio of a number of scatter events occurring within the second energy window to a number of scatter events occurring within the first energy window.

5. The method of claim 4, wherein the first ratio and the second ratio are pre-calculated and stored in a memory prior to obtaining the list mode data from the scan performed using the radiation diagnosis apparatus.

6. The method of claim 5, further comprising estimating the first ratio and the second ratio from phantom data obtained either experimentally or via simulation.

7. The method of claim 1, further comprising calculating a coincidence scatter fraction from the calculated singles scatter fraction.

8. The method of claim 7, further comprising:
  normalizing an estimated scatter sinogram using the calculated coincidence scatter fraction; and
  performing scatter correction using the normalized scatter sinogram.

9. The method of claim 1, wherein the calculating step further comprises calculating, for each crystal in the radiation diagnostic apparatus, a per-crystal singles scatter fraction; and
  the method further includes
    determining, from the calculated per-crystal singles scatter fractions, a first map and a second map, the first map indicating, for each of a plurality of lines of response (LORs), a fraction of single-scattered coincidence events, and the second map indicating, for each of the LORs, a fraction of double-scattered coincidence events;
    estimating a coincidence scatter fraction from the determined first and second maps; and
    using the estimated coincidence scatter fraction directly in a reconstruction process to reconstruct the image from the list mode data.

10. The method of claim 9, wherein the step of determining the first map and the second map comprises performing an iterative optimization process to minimize a cost function that is based on the calculated per-crystal singles scatter fractions.

11. The method of claim 1, wherein the calculating step further comprises calculating, for each group of a plurality of groups of crystals in the radiation diagnostic apparatus, a singles scatter fraction for the group.

12. The method of claim 1, wherein the step of acquiring the energy spectrum further comprises subtracting random events from an initial energy spectrum.

13. An apparatus for determining a scatter fraction for a radiation diagnosis apparatus, the apparatus comprising:
  circuitry configured to
    acquire an energy spectrum from list mode data obtained from a scan performed using the radiation diagnosis apparatus;
    determine, from the acquired list mode data, a first number of events occurring in a first energy window spanning a first energy range;
    determine, from the acquired list mode data, a second number of events occurring in a second window, the second energy window spanning a second energy range different from the first energy range;
    calculate a singles scatter fraction based on the determined first number of events and the determined second number of events and
    reconstruct an image based on the acquired list mode data and the calculated singles scatter fraction.

14. The apparatus of claim 13, wherein the circuitry is further configured to, in determining the first number of events, determine the first number of events occurring in the first energy window, which is a photopeak energy window that includes a photopeak energy level.

15. The apparatus of claim 14, wherein the circuitry is further configured to, in determining the second number of events, determine the second number of events occurring in the second energy window spanning the second energy range, which lies entirely above the photopeak energy level.

16. The apparatus of claim 13, wherein
the circuitry is further configured to, in calculating the singles scatter fraction, calculate the singles scatter fraction further based on a first ratio and a second ratio;
the first ratio is a ratio of a number of true events occurring within the second energy window to a number of true events occurring within the first energy window; and
the second ratio is a ratio of a number of scatter events occurring within the second energy window to a number of scatter events occurring within the first energy window.

17. The apparatus of claim 16, further comprising a memory, wherein the first ratio and the second ratio are pre-calculated and stored in the memory prior to obtaining the list mode data from the scan performed using the radiation diagnosis apparatus.

18. The apparatus of claim 17, wherein the circuitry is further configured to estimate the first ratio and the second ratio from phantom data obtained either experimentally or via simulation.

19. The apparatus of claim 13, wherein the circuitry is further configured to calculate a coincidence scatter fraction from the calculated singles scatter fraction.

20. A system, comprising:
a radiation diagnosis apparatus configured to perform a scan of a patient to obtain list mode data; and
circuitry configured to
acquire an energy spectrum from the obtained list mode data;
determine, from the acquired list mode data, a first number of events occurring in a first energy window spanning a first energy range;
determine, from the acquired list mode data, a second number of events occurring in a second window, the second energy window spanning a second energy range different from the first energy range;
calculate a singles scatter fraction based on the determined first number of events and the determined second number of events and
reconstruct an image based on the acquired list mode data and the calculated singles scatter fraction.

* * * * *